United States Patent [19]

Martel et al.

[11] Patent Number: 4,501,687
[45] Date of Patent: Feb. 26, 1985

[54] CYCLOPENTANOLS

[75] Inventors: Jacques Martel, Bondy; Jean Buendia, Le Perreux; Francois Nezot, Thiais, all of France

[73] Assignee: Roussel Uclaf, Paris, France

[21] Appl. No.: 325,992

[22] Filed: Nov. 30, 1981

[30] Foreign Application Priority Data

Dec. 5, 1980 [FR] France ............... 80 25869

[51] Int. Cl.³ .............. A61K 7/46; C07C 35/06
[52] U.S. Cl. ................ 252/522 R; 560/122; 562/504; 568/662; 568/670; 568/838
[58] Field of Search ............ 560/122, 261, 121; 568/420, 838, 448, 675, 579, 670, 679, 662; 252/522, 522 A; 562/504

[56] References Cited

U.S. PATENT DOCUMENTS

| | | | |
|---|---|---|---|
| 2,934,560 | 4/1960 | Kimel | 568/838 |
| 3,057,888 | 10/1962 | Marbet et al. | 568/448 |
| 3,217,041 | 11/1965 | Houlihan | 568/838 |
| 3,238,260 | 3/1966 | Pasedach et al. | 568/670 |
| 3,256,320 | 6/1966 | Dowbenko | 568/670 |
| 3,933,892 | 1/1976 | Chadha et al. | 568/838 |
| 3,937,723 | 2/1976 | Schulte-Elte | 568/838 |
| 4,052,341 | 10/1977 | Naipawer et al. | 568/838 |
| 4,069,258 | 1/1978 | Hoffman et al. | 568/838 |
| 4,127,736 | 11/1978 | Chadha et al. | 568/838 |
| 4,149,020 | 4/1979 | Kamath et al. | 568/838 |

OTHER PUBLICATIONS

Demole et al., "Chemical Abstracts" vol. 57, (1962), p. 16386.
Meinwald et al., "J. Amer. Chem. Soc." vol. 82, (1960), pp. 5235–5239.
Sauer, "J.A.C.S." vol. 81, 1959, p. 925.
English et al., "J. Amer. Chem. Soc." vol. 75, (1920), pp. 1909–1912.

Primary Examiner—Werren B. Lone
Attorney, Agent, or Firm—Charles A. Muserlian

[57] ABSTRACT

Novel cyclopentanols of the formula

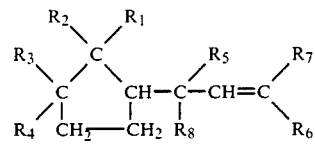

wherein $R_1$ and $R_2$ are identical and are selected from the group consisting of hydrogen and alkyl of 1 to 4 carbon atoms, $R_3$ is selected from the group consisting of —OH, alkoxy of 1 to 8 carbon atoms and acyloxy of an organic carboxylic acid of 1 to 18 carbon atoms, $R_4$ is selected from the group consisting of hydrogen and alkyl of 1 to 8 carbon atoms, $R_5$ and $R_8$ are individually selected from the group consisting of hydrogen, alkyl of 1 to 8 carbon atoms and alkenyl and alkynyl of 2 to 8 carbon atoms and $R_6$ and $R_7$ are individually selected from the group consisting of hydrogen, alkyl of 1 to 8 carbon atoms, alkenyl and alkynyl of 2 to 8 carbon atoms, —CN, —COCH$_3$ and —COOAlK$_2$ and AlK$_2$ is alkyl of 1 to 8 carbon atoms useful as perfumery agents and their preparation and novel intermediates.

8 Claims, No Drawings

CYCLOPENTANOLS

OBJECTS OF THE INVENTION

It is an object of the invention to provide the novel compounds of formula I and a novel process for their preparation and novel intermediates.

It is another object of the invention to provide novel perfume compositions and to provide a novel method of imparting a pleasant smell to a composition.

These and other objects and advantages of the invention will become obvious from the following detailed description.

THE INVENTION

The novel compounds of the invention are cyclopentanols of the formula

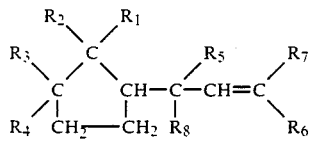

wherein $R_1$ and $R_2$ are identical and are selected from the group consisting of hydrogen and alkyl of 1 to 4 carbon atoms, $R_3$ is selected from the group consisting of —OH, alkoxy of 1 to 8 carbon atoms and acyloxy of an organic carboxylic acid of 1 to 18 carbon atoms, $R_4$ is selected from the group consisting of hydrogen and alkyl of 1 to 8 carbon atoms, $R_5$ and $R_8$ are individually selected from the group consisting of hydrogen, alkyl of 1 to 8 carbon atoms and alkenyl and alkynyl of 2 to 8 carbon atoms and $R_6$ and $R_7$ are individually selected from the group consisting of hydrogen, alkyl of 1 to 8 carbon atoms, alkenyl and alkynyl of 2 to 8 carbon atoms, —CN, —COCH$_3$ and —COOAlK$_2$ and AlK$_2$ is alkyl of 1 to 8 carbon atoms.

Examples of $R_1$ and $R_2$ are hydrogen and alkyl, preferably methyl, ethyl or propyl. Examples of $R_3$ are hydroxyl, alkoxy of 1 to 8 carbon atoms such as methoxy, ethoxy, n-propoxy, isopropoxy and n-butoxy and acyloxy of an organic carboxylic acid of 1 to 18 carbon atoms such as optionally unsaturated aliphatic and cycloaliphatic carboxylic acids such as alkanoic acids like formic acid, acetic acid, propionic acid, butyric acid, isobutyric acid or undecylic acid, or hydroxy alkanoic acids like hydroxyacetic acid; or cycloalkyl carboxylic acids or cycloalkylalkanoic acids like cyclopropyl carboxylic acid, cyclopentyl carboxylic acid, cyclohexylcarboxylic acid, cyclopentylacetic acid, cyclohexylacetic acid, cyclopentylpropionic acid or cyclohexylpropionic acid; benzoic acid or phenylalkanoic acids such as phenylacetic acid or phenylpropionic acid; or amino acids such as diethylaminoacetic acid or aspartic acid.

When $R_4$, $R_5$, $R_6$, $R_7$ or $R_8$ are alkyl, they are preferably alkyl of 1 to 6 carbon atoms such as methyl, ethyl, n-propyl, isopropyl, pentyl, butyl or hexyl. When $R_5$, $R_6$, $R_7$ or $R_8$ are alkenyl, they are preferably vinyl, allyl, 2-methylallyl or isobutenyl. When $R_5$, $R_6$, $R_7$ or $R_8$ are alkynyl, they are preferably ethynyl, 1-propynyl, 2-propynyl or 2-butynyl. When $R_6$ or $R_7$ is —COOAlK$_2$, AlK$_2$ is preferably methyl, ethyl, propyl, isopropyl or butyl.

Among the preferred compounds of formula I are those wherein $R_1$ and $R_2$ are hydrogen, those wherein $R_1$ and $R_2$ are methyl, those wherein $R_4$ is hydrogen or methyl, those wherein $R_3$ is —OH or

and those wherein $R_5$ and $R_8$ are hydrogen.

The novel process of the invention for the preparation of compounds of formula I comprises subjecting a compound of the formula

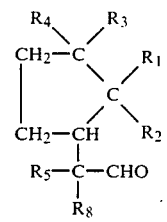

wherein $R_1$, $R_2$, $R_3$, $R_4$, $R_5$ and $R_8$ have the above definitions in its aldehyde or hemiacetal form to the Wittig reaction with a compound of the formula

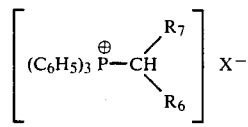

wherein $R_6$ and $R_7$ have the above definitions and $X^-$ is a halide ion to obtain the corresponding compound of formula I which if $R_3$ is —OH, may be reacted with an esterification agent or an etherification agent.

In a preferred mode of the process, X is bromine, chlorine or iodine and the Wittig reaction is effected in an organic solvent selected from the group consisting of dimethylformamide, dimethylsulfoxide, tetrahydrofuran, ether, monoethyl ether of diethyleneglycol, diethyl ether of diethyleneglycol or benzene in the presence of a strong base selected from the group consisting of alkali metal hydrides, alkali metal amides, alkali metal alcoholates and butyllithium.

The etherification of the compounds of formula I when $R_3$ is OH may be effected by classical methods such as forming the sodium derivative of the compound of formula I and reacting the latter with an alkyl halide of 1 to 8 alkyl carbons. The esterification of the compounds of formula I when $R_3$ is —OH may be effected by reacting the latter with a functional acid derivative such as the acid chloride or acid anhydride or with the free acid in the presence of dicyclohexylcarbodiimide or diisopropylcarbodiimide.

In one variation of the process of the invention, a compound of formula II is reacted with a compound of the formula

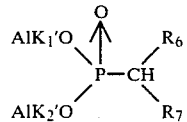

wherein $R_6$ and $R_7$ have the above definition and AlK$_1'$ and AlK$_2'$ are alkyl of 1 to 8 carbon atoms. This variation of the process is particularly useful when $R_6$ and $R_7$ are other than alkyl.

In another variation of the process of the invention, a compound of formula II in its aldehyde or hemiacetal form is reacted with a compound of the formula

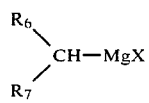

wherein $R_6$ and $R_7$ have the above definition and X is a halogen to obtain a compound of the formula

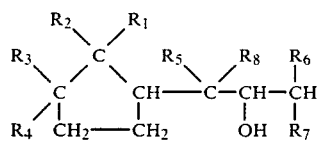

and reacting the latter with a dehydration agent to form the corresponding compound of formula I. The dehydration is preferably effected by heating in an acid medium.

The compounds of formula II are novel intermediates and are a part of the invention. The compounds of formula II wherein $R_3$ is —OH may be prepared by reacting a compound of the formula

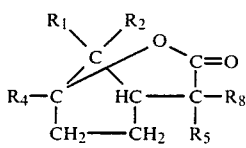

with a hydrogenation agent such as diisobutylaluminum hydride at a low temperature such as $-40°$ to $-60°$ C. The compounds of formula II wherein $R_3$ is —OH may be esterified or etherified by the procedure indicated above.

The compounds of formula VI are known compounds which may be prepared by the processes described by Meinwald [J.A.C.S., Vol. 82 (1960), p. 5235] or by Ronald et al [J.A.C.S., Vol 81 (1959), p. 925].

The compounds of formula V produced in the variation of the process of the invention are also novel intermediates and are a part of the invention.

The novel odorant compositions of the invention are comprised of an odorantly effective amount of at least one compound of formula I and a carrier. The compositions have an agreable odor such as a floral odor, a flowery odor, a fruity odor, a spice odor or a woody odor.

The compositions may be used as odorants in perfumes or to prepare odorant compositions which serve as perfume bases. They are also useful in the preparation of hygienic compositions such as soaps, talcum powders, shampoos, dentifrices, bath salts, bath oils or bubble baths, deodorants or in the preparation of cosmetic products such as cremes, makeup milks, lotions, face paint, lipsticks and nail polishes. The compositions may also be used in detergent compositions such as washing powders or the preparation of maintenance products such as waxes or the preparation of insecticides.

The compounds of formula I may be used to impart a pleasant odor to products lacking any odor or to raise up, exalt or modify the odor of compositions having their own odor. They may also be used to mask a disagreeable odor of a product. Naturally, the perfumes, hygienic products, cosmetics, detergent products and maintenance products are prepared by the usual techniques employed in these industries which are largely described in the literature.

The compositions of the invention may contain other usual ingredients such as support vehicles, modifiers, fixing agents, preservatives, stabilizers and other ingredients such as supports, solvents, dispersants and emulsifiers usually used.

When the compounds of formula I are used in perfumes, a small amount of the compound of formula I is added to other components well known in the perfumery art which may be natural products such as vetiver essence, cedar essence, bergamot orange essence, pine needle essence, lemon essence, jasmin or mandarin orange essence or may be synthetic products such as aldehydes commonly used in perfumery such as hydroxy-citronellal, ketones such as α-ionone, phenolic compounds such as eugenol, alcohols such as geraniol or lactones such as coumarine.

The amounts of the compounds of formula I used in perfumes will vary greatly as a function of the nature of the specific compound, the use one wishes to make, the intensity of the odor desired as well as, naturally, the nature and composition of the other ingredients added thereto. In perfumes, there may be used 0.1 to 10 parts by weight of the compounds of formula I per 100 parts by weight of the compositions and when used in a perfume base, the base may contain up to 20% by weight of the compound of formula I. When used in detergents, 0.1 to 2 parts by weight of the compounds of formula I per 100 parts by weight of the detergent composition may be used.

The normal method of the invention for imparting a pleasant odor to a composition comprises incorporating into a composition an odorantly effective amount of at least one compound of formula I.

In the following examples there are described several preferred embodiments to illustrate the invention. However, it is to be understood that the invention is not intended to be limited to the specific embodiments.

EXAMPLE 1

3-(2-propenyl)-cyclopentanol

STEP A: 3-hydroxycyclopentyl-acetaldehyde 55 ml of a solution of 1.2M diisobutyl aluminum hydride in toluene were added dropwise at $-60°$ C. to a solution of 8 g of 2-oxa-bicyclo-[3,2,1]-3-octanone [described by Meinwald, J.A.C.S., Vol. 82 (1960), p. 5235] in toluene and the mixture was stirred at $-60°$ C. for 15 minutes and was then poured into iced N hydrochloric acid solution. The decanted organic phase was dried and evaporated to dryness under reduced pressure at less than 25° C. to obtain 0.8 g of product. The wash waters were extracted with methylene chloride to obtain another 7 g of product. The combined 7.8 g of product was chromatographed over silica gel and was eluted with a 1—1 benzene-ethyl acetate mixture to obtain 6 g of 3-hydroxycyclopentyl-acetaldehyde.

NMR Spectrum (deuterochloroform): Peaks at 4.5 ppm (hydrogens of 3-carbon of cyclopentane); at 9.8 ppm (hydrogen of formyl).

STEP B: 3-(2-propenyl)-cyclopentanol

A solution of 5 g of potassium tert.-butylate in 80 ml of dimethylformamide was added at −60° C. over 90 minutes to a solution of 5 g of 3-hydroxy-cyclopentyl-acetaldehyde, 15 g of triphenyl methyl phosphonium bromide and 100 ml of dimethylformamide and the resulting suspension was stirred at −60° C. for 2 hours after which the temperature was allowed to rise to 20° C. The mixture was poured into 2N hydrochloric acid solution and the mixture was extracted with isopropyl ether. The organic phase was dried and evaporated to dryness under reduced pressure. The residue was chromatographed over silica gel and was eluted with a 7–3 cyclohexane-ethyl acetate mixture to obtain 1.7 g of 3-(2-propenyl)-cyclopentanol.

NMR Spectrum (deuterochloroform): Peaks at 1.6 ppm (hydrogen of —OH); at 3.7 ppm (hydrogens on carbon attached to —OH); at 5.4 to 6.2 ppm (hydrogen of 2-carbon of propenyl); at 4.75 to 5.2 ppm (hydrogens of 3-carbon of propenyl).

EXAMPLE 2

3-(3-methyl-2-butenyl)-cyclopentanol

Using the procedure of Example 1, 10 g of 3-hydroxycyclopentyl-acetaldehyde and 37 g of triphenyl 1-methyl ethyl phosphonium iodide were reacted to obtain 8 g of residue which were chromatographed over silica gel. Elution with a 7–3 cyclohexane-ethyl acetate mixture yielded 2 g of 3-(3-methyl-2-butenyl)-cyclopentanol.

NMR Spectrum (deuterochloroform): Peaks at 2 ppm (hydrogen of —OH); at 4.2–4.25–4.3 ppm (hydrogens on carbon attached to —OH); at 1.6–1.7 ppm (hydrogens of methyls of 3-methyl-2-butenyl); at 5–5.2–5.4 ppm (hydrogens on 2-carbon of 3-methyl-2-butenyl).

EXAMPLE 3

3-(2-butenyl)cyclopentanol

A solution of 7 g of potassium tert.-butylate in 15 ml of dimethylformamide was added over 30 minutes at 20° C. to a solution of 5 g of 3-hydroxy-cyclopentyl-acetaldehyde, 20 g of triphenyl ethyl phosphonium bromide and 20 ml of dimethylformamide and the mixture was stirred at 20° C. for 17 hours and then poured into 2N hydrochloric acid solution. The mixture was extracted with isopropyl ether and the organic phase was washed with water, dried and evaporated to dryness to obtain a residue. The latter was chromatographed over silica gel and was eluted with an 8–2 cyclohexane-ethyl acetate mixture to obtain 2 g of 3-(2-butenyl)-cyclopentanol.

NMR Spectrum (deuterochloroform): Peaks at 4.25 ppm (hydrogens of carbon attached to —OH); at 5.4 ppm (hydrogens of 2- and 3-carbons of butenyl); at 1.58–1.65 ppm (hydrogens of 4-carbon of butenyl).

EXAMPLE 4

3-(2-pentenyl)-cyclopentanol

Using the procedure of Example 3, 5 g of 3-hydroxy cyclopentyl-acetaldehyde and 20 g of triphenyl propyl phosphonium bromide were reacted and the product was chromatographed over silica gel. Elution with a 7–3 cyclohexane-ethyl acetate mixture yielded 1.5 g of 3-(2-pentenyl)-cyclopentanol.

NMR Spectrum (deuterochloroform): Peaks at 4.22 ppm (hydrogens on carbon attached to —OH); at 5.3 ppm (hydrogens on 2- and 3-carbons of pentenyl); at 0.83–0.95–1.07 ppm (hydrogens of 5-carbon of pentenyl).

EXAMPLE 5

3-(2-hexenyl)-cyclopentanol

Using the procedure of Example 3, 5 g of 3-hydroxy cyclopentyl-acetaldehyde and 20 g of triphenyl butyl phosphonium bromide were reacted and the product was chromatographed over silica gel. Elution with a 7–3 cyclohexane-ethyl acetate mixture yielded 1.4 g of 3-(2-hexenyl)-cyclopentanol.

NMR Spectrum (deuterochloroform): Peaks at 4.2 ppm (hydrogens of carbon attached to —OH); at 5.3 ppm (ethylenic hydrogens); at 0.78–0.9–1.2 ppm (hydrogens of 6-carbon of hexenyl).

EXAMPLE 6

1-acetyloxy-3-(2-butenyl)-cyclopentane

A solution of 2 ml of acetyl chloride in 5 ml of benzene was added at 0° C. to a solution of 1 g of 3-(2-butenyl)-cyclopentanol in 20 ml of benzene and 2 ml of pyridine and the mixture was stirred at 20° C. for 17 hours and was poured into 2N hydrochloric acid solution with stirring. The decanted aqueous phase was extracted with benzene and the organic phase was washed with water, dried and evaporated to dryness. The residue was chromatographed over silica gel and was eluted with a 9–1 cyclohexane-ethyl acetate mixture to obtain 1.4 g of 1-acetyloxy-3-(2-butenyl)-cyclopentane.

NMR Spectrum (deuterochloroform): Peaks at 5.13 ppm (hydrogens on carbon attached to acetyloxy); at 2.03 ppm (hydrogens of

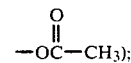

at 5.4 ppm (hydrogens of 2- and 3-carbons of butenyl); at 1.6–1.7 ppm (hydrogens of 4-carbon of butenyl).

EXAMPLE 7

(1R,S) 1,2,2-trimethyl-3-(2-propenyl)-cyclopentanol

STEP A: 1,8,8-trimethyl-2-oxa-bicyclo [3,2,1] octan-3-ol 25 ml of a solution of 1.1M of diisobutylaluminum hydride in toluene was added at −60° C. over 90 minutes to a solution of 5 g of 1,8,8-trimethyl-2-oxa-bicyclo [3,2,1] octane-3-one [process of Ronald et al, J.A.C.S., Vol. 81 (1959), p. 925] in 20 ml of toluene and the mixture was stirred for 2 hours at −60° C. Water was added dropwise while the temperature was allowed to rise to 20° C. and the mixture was then stirred at 20° C. for 2 hours. The mixture was filtered to remove lithium salts and the filter was washed with methylene chloride. The decanted aqueous phase of the filtrate was extracted with methylene chloride. The organic phase was dried and evaporated to dryness and the residue was chromatographed over silica gel. Elution with a 1—1 benzene-ethyl acetate mixture yielded 3.5 g of 1,8,8-trimethyl-2-oxa-bicyclo [3,2,1] octan-3-ol.

NMR Spectrum (deuterochloroform): Peaks at 0.85 and 1.1 ppm (hydrogens of 1 and 8 methyls); at 3.4–3.5 ppm (hydrogen of —OH); at 5 to 5.4 ppm (hydrogens of 3-carbon).

STEP B: (1R,S) 1,2,2-trimethyl-3-(2-propenyl)-cyclopentanol

A solution of 4 g of potassium tert.-butylate in 15 ml of dimethylformamide was added over 90 minutes to a solution of 5 g of the product of Step A, 15 g of triphenyl methyl phosphonium bromide and 20 ml of dimethylformamide and the mixture was stirred at 20° C. for 2 hours and was then poured into 2N hydrochloric acid solution. The mixture was extracted with isopropyl ether and the organic phase was washed with water, dried and evaporated to dryness. The residue was chromatographed over silica gel and was eluted with a 8–2 cyclohexane-ethyl acetate mixture to obtain (1R,S) 1,2,2-trimethyl-3-(2-propenyl)-cyclopentanol NMR Spectrum (deuterochloroform): Peaks at 1.2 ppm (hydrogens of —CH$_3$ attached to —OH); at 0.83 and 0.88 ppm (hydrogens of 2-methyls of cyclopentanol); at 5.5 to 6.2 ppm (hydrogens of 2-carbon of propenyl); at 4.8 to 5.2 ppm (hydrogens of 3-carbon of propenyl).

EXAMPLE 8

(1R,S) 1,2,2-trimethyl-3-(5-methyl-2,4-hexenyl)-cyclopentanol

Using the procedure of Example 7, 16 g of 3-methyl-2-butenyl triphenyl phosphonium chloride and 5 g of 1,8,8-trimethyl-2-oxa-bicyclo [3,2,1] octan-3-ol were reacted and the product was chromatographed over silica gel and was eluted with an 8–2 cyclohexane-ethyl acetate mixture to obtain 1.7 g of (1 R,S) 1,2,2-trimethyl-3-(5-methyl-2,4-hexenyl)-cyclopentanol.

NMR Spectrum (deuterochloroform): Peaks at 0.87 ppm (hydrogens of 2-methyls); at 1.17 ppm (hydrogens of 1-CH$_3$ of cyclopentanol); at 4.8 to 7.3 ppm (hydrogens of 2,3 and 4 carbons of 2,4-hexenyl); at 1.73–1.8 ppm (hydrogens of —CH$_3$ of 5-methyl-2,4-hexenyl).

EXAMPLE 9

(1R,S) 1,2,2-trimethyl-3-(2-butenyl)-cyclopentanol

Using the procedure of Example 7, 5 g of 1,8,8-trimethyl-2-oxa bicyclo [3,2,1] octan-3-ol and 15 g of triphenyl ethyl phosphonium bromide were reacted and the product was chromatographed over silica gel and was eluted with an 8–2 cyclohexane-ethyl acetate mixture to obtain 4 g of (1R,S) 1,2,2-trimethyl-3-(2-butenyl)-cyclopentanol.

NMR Spectrum (deuterochloroform): Peaks at 1.17 ppm (hydrogens of 1-CH$_3$); at 0.85 ppm (hydrogens of 2-methyls); at 5.4 ppm (hydrogens of 2- and 3-carbons of butenyl); at 1.6 to 1.7 ppm (hydrogens of 4-carbon of butenyl).

EXAMPLE 10

(1R,S) 1,2,2-trimethyl-3-(3-methyl-2-butenyl)-cyclopentanol

Using the procedure of Example 7, 5 g of 1,8,8-trimethyl-2-oxa bicyclo [3,2,1] octan-3-ol and 15 g of triphenyl isopropyl phosphonium iodide were reacted and the product was chromatographed over silica gel and was eluted with an 8–2 cyclohexane-ethyl acetate mixture to obtain 4.1 g of (1R,S) 1,2,2-trimethyl-3-(3-methyl-2-butenyl)-cyclopentanol.

NMR Spectrum (deuterochloroform): Peaks at 0.83 and 0.86 ppm (hydrogens of 2-methyls); at 1.18 ppm (hydrogens of 1-CH$_3$); at 1.62–1.68 ppm (hydrogens of methyls of 3-methyl-2-butenyl).

EXAMPLE 11

(1R,S) 1,2,2-trimethyl-3-(2-pentenyl)-cyclopentanol

Using the procedure of Example 7, 5 g of 1,8,8-trimethyl-2-oxa bicyclo [3,2,1] octan-3-ol and 15 g of triphenyl propyl phosphonium bromide were reacted and the product was chromatographed over silica gel and was eluted with an 8–2 cyclohexane-ethyl acetate mixture to obtain 4 g of (1R,S) 1,2,2-trimethyl-3-(2-pentenyl)-cyclopentanol.

NMR Spectrum (deuterochloroform): Peaks at 0.83 and 0.86 ppm (hydrogens of 2-methyls); at 1.17 ppm (hydrogens of 1-CH$_3$); at 5.33 ppm (ethylenic hydrogens of pentenyl); at 0.83–0.93–1.05 ppm (hydrogens of 5-carbon of pentenyl).

EXAMPLE 12

(1R,S) 1,2,2-trimethyl-3-(2-hexenyl)-cyclopentanol

Using the procedure of Example 7, 5 g of 1,8,8-trimethyl-2-oxa bicyclo [3,2,1] octan-3-ol and 15 g of triphenyl butyl phosphonium bromide were reacted and the product was chromatographed over silica gel and was eluted with an 8–2 cyclohexane-ethyl acetate mixture to obtain 4 g of (1R,S) 1,2,2-trimethyl-3-(2-hexenyl)-cyclopentanol.

NMR Spectrum (deuterochloroform): Peaks at 0.87 and 0.9 ppm (hydrogens of 2-methyls); at 1.2 ppm (hydrogens of 1-CH$_3$); at 5.5 ppm (hydrogens of 2- and 3-carbons of hexenyl); at 0.85–0.95–1.05 ppm (hydrogens of 6-carbon of hexenyl).

EXAMPLE 13

(1R,S) 1,2,2-trimethyl-3-(3-methyl-2-butenyl-4-methoxycarbonyl)-cyclopentanol 8 g of 0,0-diethyl 1-methoxycarbonyl ethyl phosphonate were added at 0° C. over 15 minutes to a solution of 2 g of sodium methylate in 10 ml of methanol and then a solution of 5 g of 1,8,8-trimethyl-2-oxa bicyclo [3,2,1] octan-3-ol in 5 ml of benzene was added over 90 minutes to the mixture. The reaction mixture was stirred for 3 hours at 20° C. and was then poured into 2N hydrochloric acid solution. The decanted aqueous phase was extracted with benzene and the organic phase was washed with water, dried and evaporated to dryness. The residue was chromatographed over silica gel and was eluted with an 8–2 benzene-ethyl acetate mixture to obtain 2 g of (1 R,S) 1,2,2-trimethyl-3-(3-methyl-2-butenyl-4-methoxycarbonyl)-cyclopentanol.

NMR Spectrum (deuterochloroform): Peaks at 0.87 ppm (hydrogens of 2-methyls); at 1.37 ppm (hydrogen of OH); at 1.17 ppm (hydrogens of 1-CH$_3$); at 6,6–6.7–6.8 ppm (hydrogens of 2-carbon of 3-methyl-2-butenyl); at 3.72 ppm (hydrogen of —COOCH$_3$); at 1.83 ppm (hydrogens of 3-CH$_3$).

EXAMPLE 14

(1R,S) 1,2,2-trimethyl-3-(2(E)-propenyl-3-ethoxy-carbonyl)-cyclopentanol

A solution of 12 g of triphenyl ethoxycarbonyl methylene phosphorane, 5 g of 1,8,8-trimethyl-2-oxa bicyclo [3,2,1] octan-3-ol and 50 ml of anhydrous benzene was refluxed for 3 hours and the benzene was distilled. The residue was taken up in isopropyl ether and the solution was vacuum filtered to remove insolubles. The filter was washed with isopropyl ether and the filtrate was evaporated to dryness. The residue was chromatographed over silica gel and was eluted with an 8-2 benzene-ethyl acetate mixture to obtain 1.5 g of (1R,S) 1,2,2-trimethyl-3-(2(E)-propenyl-3-ethoxy-carbonyl)-cyclopentanol.

NMR Spectrum (deuterochloroform): Peaks at 0.85 and 0.87 ppm (hydrogens of 2-methyls); at 1.18 ppm (hydrogens of 1-CH$_3$); at 6.7–6.8–6.9 ppm and 6.9–7–7.1 ppm (hydrogens of 2-carbon of propenyl); at 1.17–1.28–1.4 ppm and 4–4.1–4.2 ppm (hydrogens of COOCH$_2$—CH$_3$); at 5.7–5.9 ppm (hydrogens of 3-carbon of propenyl).

EXAMPLE 15

(1R,S) 1,2,2-trimethyl-1-acetyloxy-3-(2-hexenyl)-cyclopentane

A mixture of 2 g of (1R,S) 1,2,2-trimethyl-3-(2-hexenyl)-cyclopentanol, 100 ml of benzene, 30 ml of pyridine and 20 ml of acetyl chloride was refluxed for 3 hours and was then cooled to 20° C. and poured into 2N hydrochloric acid solution. The decanted aqueous phase was extracted with benzene and the organic phase was dried and evaporated to dryness. The residue was chromatographed over silica gel and was eluted.

NMR Spectrum (deuterochloroform): Peaks at 0.85–0.93 ppm (hydrogens of 2-methyls); at 1.38 ppm (hydrogens of 1-CH$_3$); at 1.98 ppm (hydrogens of acetoxy); at 5.33 ppm (hydrogens of 2- and 3-carbons of hexenyl); at 0.92 ppm (hydrogens of 6-carbon of hexenyl).

EXAMPLE 16

(1R,S) 1,2,2-trimethyl-1-acetyloxy-3-(2-butenyl)-cyclopentane

Using the procedure of Example 15, 2 g of (1R,S) 1,2,2-trimethyl-3-(2-butenyl)-cyclopentanol and 15 ml of acetyl chloride were reacted to obtain 1.8 g of (1R,S) 1,2,2-trimethyl-1-acetyloxy-3-(2-butenyl)-cyclopentane.

NMR Spectrum (deuterochloroform): Peaks at 0.85 and 0.93 ppm and 0.82 and 0.92 ppm (hydrogens of 2-methyls); at 1.38 ppm (hydrogens of 1-CH$_3$); at 1.98 ppm (hydrogens of

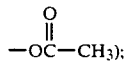

at 5.3 ppm (hydrogens of 2- and 3-carbons of butenyl); at 1.56–1.65 ppm (hydrogens of 4-carbon of butenyl).

EXAMPLE 17

(1R,S) 1,2,2-trimethyl-1-acetyloxy-3-(2-propenyl)-cyclopentane

Using the procedure of Example 15, 1.6 g of 1,2,2-trimethyl-3-(2-propenyl)-cyclopentanol and 10 ml of acetyl chloride were reacted to obtain 1.3 of (1R,S) 1,2,2-trimethyl-1-acetyloxy-3-(2-propenyl)-cyclopentane.

NMR Spectrum (deuterochloroform): Peaks at 0.83 and 0.93 ppm (hydrogens of 2-methyls); at 1.38 ppm (hydrogens of 1-CH$_3$); at 1.98 ppm (hydrogens of acetoxy); at 5.5 to 6.25 ppm (hydrogens of 2-carbon of propenyl); at 4.8 to 5.2 ppm (hydrogens of 3-carbon of propenyl).

EXAMPLE 18

(1R,S) 1,2,2-trimethyl-1-acetyloxy-3-(3-methyl-2-butenyl)-cyclopentane

Using the procedure of Example 15, 2 g of (1R,S) 1,2,2-trimethyl-3-(3-methyl-2-butenyl)-cyclopentanol and 3 ml of acetyl chloride were reacted and the product was chromatographed over silica gel and was eluted with a 95–5 cyclohexane-ethyl acetate mixture to obtain 1.5 g of (1R,S) 1,2,2-trimethyl-1-acetyloxy-3-(3-methyl-2-butenyl)-cyclopentane.

NMR Spectrum (deuterochloroform): Peaks at 0.83 and 0.92 ppm (hydrogens of 2-methyls); at 1.37 ppm (hydrogens of 1-CH$_3$); at 1.98 ppm (hydrogens of acetoxy); at 4.9–5.1–5.3 ppm (hydrogens of 2-carbon of 3-methyl-2-butenyl); at 1.6–1.7 ppm (hydrogens of methyls of 3-methyl-2-butenyl).

EXAMPLE 19

(1R,S) 1,2,2-trimethyl-1-acetyloxy-3-(2-pentenyl)-cyclopentane

Using the procedure of Example 15, 2 g of (1R,S) 1,2,2-trimethyl-3-(2-pentenyl)-cyclopentanol and 10 ml of acetyl chloride were reacted to obtain 1.5 g of (1R,S) 1,2,2-trimethyl-1-acetyloxy-3-(2-pentenyl)-cyclopentane.

NMR Spectrum (deuterochloroform): Peaks at 0.85 and 0.93 ppm (hydrogens of 2-methyls); at 1.38 ppm (hydrogens of 1-CH$_3$); at 1.97 ppm (hydrogens of acetoxy); at 5.3 ppm (hydrogens of 2- and 3-pentenyl); at 0.85–0.95–1.05 ppm (hydrogens of 5-carbon atoms of pentenyl).

EXAMPLE 20

The odors given off by some of the products of the invention are given in the following Table.

TABLE

| Compound of Example | Odor |
| --- | --- |
| 1 | Indefinable hay odor |
| 2 | flowery acetal of lily of the valley carbinol |
| 3 | Rose |
| 4 | Rose and cucumber |
| 5 | Heavy cucumber |
| 6 | very pretty flowery, like smell of roses |
| 8 | Cedar, dry woody |
| 10 | fruity |
| 17 | Orange note |
| 18 | Bergamot orange |

EXAMPLE 21

An "Opoponax" composition was prepared containing 100 parts by weight of the product of Example 3, 310 parts by weight of bergamot orange, 20 parts by weight of synthetic neroli, 10 parts by weight of iron-free patchouli, 10 parts by weight of rose essence, 60 parts by weight of vetiverol, 125 parts by weight of Santalol, 40 parts by weight of castoreum resinoid, 80 parts by weight of coumarine, 75 parts by weight of γ-methylionone, 40 parts by weight of vanillin, 25 parts by weight of Benjoin resinoid, 40 parts by weight of musk ketone and 65 parts by weight of musk ambrette.

EXAMPLE 22

A toilet soap was prepared containing 5 parts by weight of the product of Example 2 and 1000 parts by weight of a commercial soap paste. A powdered detergent was also prepared containing 1 part of the product of Example 18 per 5000 parts of commercial powdered detergents.

Various modifications of the products and processes of the invention may be made without departing from the spirit or scope thereof and it is to be understood that the invention is intended to be limited only as defined in the appended claims.

What we claim is:

1. A method of imparting a pleasant odor to a composition comprising incorporating into a composition a sufficient amount of at least one compound of the formula

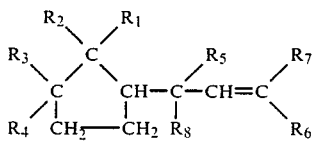

wherein $R_1$ and $R_2$ are identical and are selected from the group consisting of hydrogen and alkyl of 1 to 4 carbon atoms, $R_3$ is selected from the group consisting of —OH, alkoxy of 1 to 8 carbon atoms and acyloxy of an organic carboxylic acid of 1 to 18 carbon atoms, $R_4$ is selected from the group consisting of hydrogen and alkyl of 1 to 8 carbon atoms, $R_5$ and $R_8$ are individually selected from the group consisting of hydrogen, alkyl of 1 to 8 carbon atoms and alkenyl and alkynyl of 2 to 8 carbon atoms and $R_6$ and $R_7$ are individually selected from the group consisting of hydrogen, alkyl of 1 to 8 carbon atoms, alkenyl and alkynyl of 2 to 8 carbon atoms, —CN, —COCH$_3$ and —COOAlK$_2$ and AlK$_2$ is alkyl of 1 to 8 carbon atoms to impart a pleasant odor therein.

2. A method of claim 1 wherein $R_1$ and $R_2$ are hydrogen.

3. A method of claim 1 wherein $R_1$ and $R_2$ are methyl.

4. A method of claim 1 or 2 or 3 wherein $R_4$ is hydrogen.

5. A method of claim 1 or 2 or 3 wherein $R_4$ is methyl.

6. A method of claim 1 wherein $R_3$ is —OH or

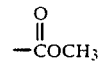

7. A method of claim 1 wherein $R_5$ and $R_8$ are hydrogen.

8. A method of claim 1 wherein the compound is selected from the group consisting of 3-(2-propenyl)-cyclopentanol, 3-(3-methyl-2-butenyl)-cyclopentanol, 3-(2-butenyl)-cyclopentanol, 3-(2-pentenyl)-cyclopentanol, 3-(2-hexenyl)-cyclopentanol, 1-acetyloxy-3-(2-butenyl)-cyclopentane, (1R,S) 1,2,2-trimethyl-3-(5-methyl-2,4-hexenyl)-cyclopentanol, (1R,S) 1,2,2-trimethyl-3-(3-methyl-2-butenyl)-cyclopentanol, (1R,S) 1,2,2-trimethyl-1-acetyloxy-3-(2-propenyl)-cyclopentane and (1R,S) 1,2,2-trimethyl-1-acetyloxy-3-(3-methyl-2-butenyl)-cyclopentane.

* * * * *